United States Patent [19]

Herrmann et al.

[11] Patent Number: 5,468,214
[45] Date of Patent: Nov. 21, 1995

[54] THERAPY APPARATUS FOR TREATMENT WITH ACOUSTIC WAVES

[75] Inventors: Klaus Herrmann, Nuernberg; Guenther Krauss, Erlangen, both of Germany

[73] Assignee: Siemens Aktiengesellschaft, Munich, Germany

[21] Appl. No.: 408,196

[22] Filed: Mar. 21, 1995

Related U.S. Application Data

[63] Continuation of Ser. No. 266,245, Jun. 27, 1994, abandoned.

[30] Foreign Application Priority Data

Jul. 27, 1993 [DE] Germany ............... 43 25 213.3

[51] Int. Cl.⁶ ............................................. A61B 17/22
[52] U.S. Cl. ........................... 601/2; 601/4; 128/660.03
[58] Field of Search .................. 601/2, 4; 128/660.03

[56] References Cited

U.S. PATENT DOCUMENTS

| | | | |
|---|---|---|---|
| 3,608,553 | 9/1971 | Balamuth | 601/2 |
| 4,669,483 | 6/1987 | Hepp et al. | 601/4 |
| 4,674,505 | 6/1987 | Pauli et al. | |
| 4,697,588 | 10/1987 | Reichenberger | |
| 4,955,365 | 9/1990 | Fry et al. | 601/2 |
| 5,018,508 | 5/1991 | Fry et al. | 601/2 |
| 5,044,354 | 9/1991 | Goldhorn et al. | 601/4 |
| 5,054,470 | 10/1991 | Fry et al. | 601/2 |
| 5,144,953 | 9/1992 | Wurster et al. | |
| 5,199,420 | 4/1993 | Artmeier | 601/4 |
| 5,207,215 | 5/1993 | Rattner et al. | |
| 5,285,772 | 2/1994 | Rattner | 128/660.03 |
| 5,301,659 | 4/1994 | Brisson et al. | 128/660.03 |
| 5,305,731 | 4/1994 | Bochholtz | 601/2 |
| 5,311,869 | 5/1994 | Okazaki | 128/660.03 |

OTHER PUBLICATIONS

Patent Abstracts of Japan, C–587, Apr. 21, 1989, vol. 13/No. 169, Application No. 62–155749.

*Primary Examiner*—Kyle L. Howell
*Assistant Examiner*—Brian L. Casler
*Attorney, Agent, or Firm*—Hill, Steadman & Simpson

[57] ABSTRACT

A therapy apparatus for treating a subject with acoustic waves has a source of acoustic waves which is adjustable in at least one degree of freedom. The apparatus includes at least one further apparatus component, which is disposed remote from the source of acoustic waves, and which is connected to the source of acoustic waves via at least one line, which may be an electrical line or a fluid line. The apparatus component is adjustable in common with the source of acoustic waves so that the distance between the source of acoustic waves and the apparatus component does not change as a consequence of the adjustment.

18 Claims, 2 Drawing Sheets

THERAPY APPARATUS FOR TREATMENT WITH ACOUSTIC WAVES

This is a continuation of application Ser. No. 08/266,245, filed Jun. 27, 1994 now abandoned.

BACKGROUND OF THE INVENTION

1. Field of the Invention

The present invention is directed to a therapy apparatus for treating a subject with acoustic waves, of the type having a source of acoustic waves which is adjustable in at least one degree of freedom with respect to a base part of the apparatus, and which has at least one further apparatus component disposed remote from the source of acoustic waves, and connected to the source of acoustic waves via at least one line.

2. Description of the Prior Art

A therapy apparatus of the type generally described above is described Patent Abstracts of Japan C-587, Apr. 21, 1989, Vol. 13, No. 169 ("Extracorporeal Treatment Apparatus"), 63-317151, and in German OS 38 40 077. The apparatus may, for example, be a lithotripter. In this known structure, the distance and/or the relative spatial orientation between the source of acoustic waves and the further apparatus component changes given an adjustment of the position of the source. This means that suitable measures must be undertaken with respect to the line that connects the source and the apparatus component to ensure that the required adjustability of the source can be accomplished without damaging the connecting line. This requires a relatively substantial equipment outlay because the connecting line may be, for example, a high-voltage line which electrically supplies the source, and must not be damaged in any case since such damage will prevent operation of the source, but more importantly such damage may present a risk to the safety of the patient and the operating personnel.

SUMMARY OF THE INVENTION

It is an object of the present invention to provide a therapy apparatus of the type generally described above, wherein the source of acoustic waves can be adjusted in the necessary manner while ensuring that the connecting line will not be damaged, with as little equipment outlay as possible and with a high degree of safety reliability.

The above object is achieved in accordance with the principles of the present invention in a therapy apparatus having a source of acoustic waves which is adjustable in at least one degree of freedom relative to a base part of the apparatus, the apparatus having at least one other apparatus component disposed remotely from the source of acoustic waves, and connected to the source of acoustic waves via at least one line, the remote apparatus component being adjustable in common with the source of acoustic waves relative to the base part so that a distance between the source and the other apparatus component does not change as a consequence of the adjustment. No measures whatsoever must be undertaken, therefore, in order to compensate for a change in distance between the source and the apparatus component. Enhanced safety is achieved because the connecting line is subjected to fewer mechanical stresses as a consequence of maintaining the constant distance between the source and the apparatus component. It is particularly beneficial when the spatial orientation of the source and the apparatus component relative to each other which exists before adjustment, is preserved unchanged during the positional adjustment. In this case, the connecting line can be constructed and arranged in the same manner as would be employed if the source were not adjustable at all. The equipment necessary for connecting the source to the apparatus component, and the degree of safety which can be achieved, are thus no less in the therapy apparatus of the invention, which permits adjustment of the source, than in the case of connecting a stationary source to a stationary apparatus component.

A therapy apparatus having a portable base part which contains apparatus components is disclosed in German OS 41 35 177. A source of acoustic waves is attached to the base part so as to be adjustable, by itself, in at least one degree of freedom. There is no common adjustability of the source and the apparatus component contained in the base part relative to the base part in the structure disclosed in OS 41 35 177.

In one embodiment of the present invention, the source and the apparatus component are attached to a carrier device, which is adjustable relative to the base part in at least one degree of freedom.

It is also known from European Application 0 483 396 to connect a high-voltage generator to a source of acoustic waves via a high-voltage cable, with the high-voltage generator being remote from the source. Normally, the significant mechanical stiffness of high-voltage cables represents a special problem in the art, for the reasons noted above, when it is desired to adjust the position of the source of acoustic waves. In the present invention, however, such a stiff high-voltage cable can be employed as the aforementioned connecting line without any difficulty.

As is also known from European Application 0 483 396, the source of acoustic waves may be connected via a fluid connecting line to a liquid reservoir and/or a liquid pump. If the source disclosed in European Application 0 483 396 were employed in a conventional therapy system, it would be necessary to employ hose conduits for the fluid connecting lines, in order to accommodate the change in distance or orientation between the source and the reservoir or pump which would occur in such a conventional system during adjustment of the position of the source. Such hose conduits are susceptible to disruption and leakage. In the therapy apparatus of the present invention, by contrast, rigid fluid lines can be employed instead, which is a more satisfactory solution.

DESCRIPTION OF THE PREFERRED EMBODIMENTS

Figure 1:
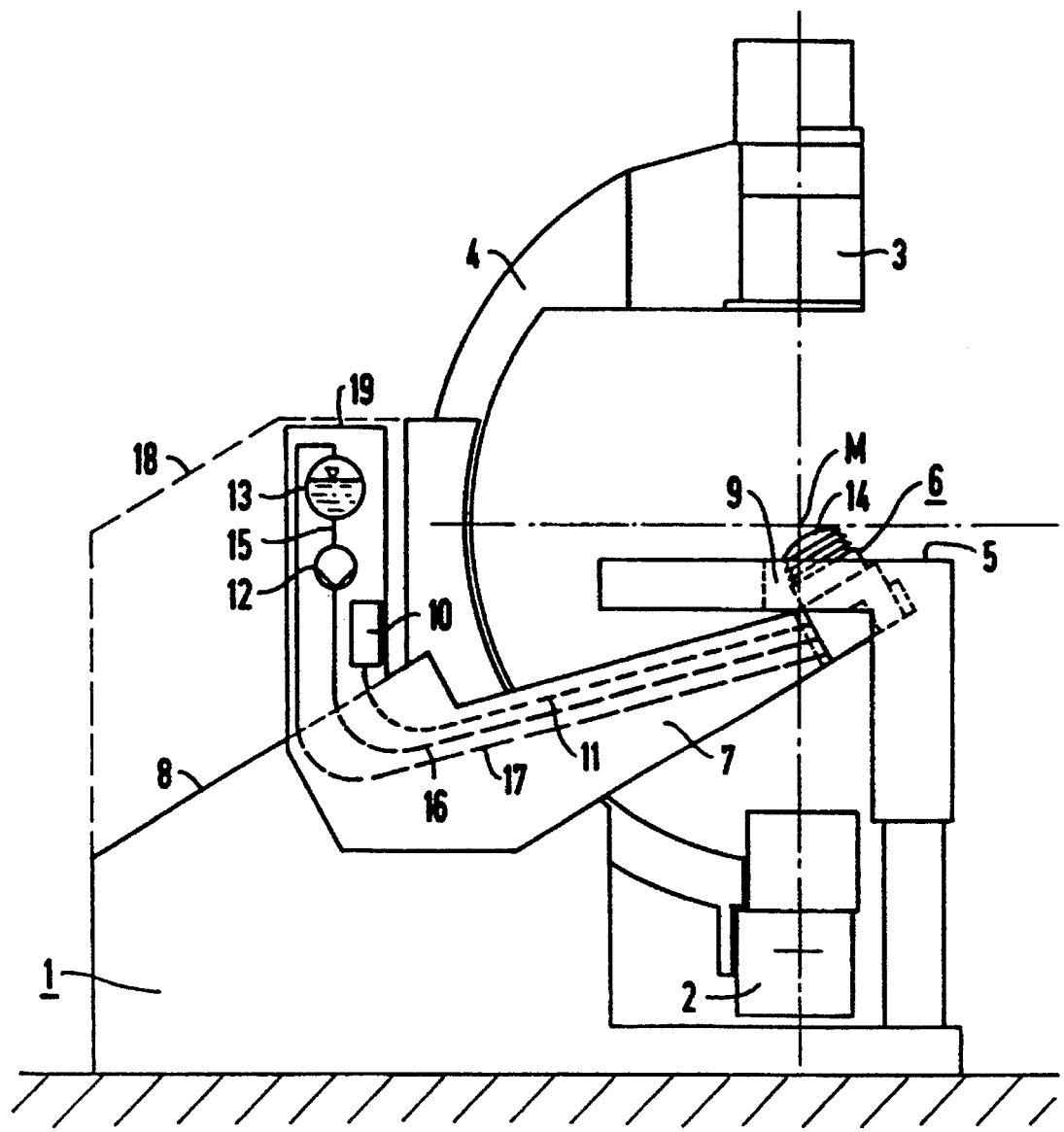
FIG. 1 is an end elevational view of a therapy apparatus constructed in accordance with the principles of the present invention in a first operating condition.

The therapy apparatus of the invention shown in FIG. 1 has a base 1 to which a x-ray locating system is attached. The x-ray locating system includes an x-ray radiator 2 and an x-ray image intensifier 3, which are respectively mounted at the opposite ends of a C-arm 4, so as to be oriented opposite one another.

The C-arm 4 is connected to the base 1 in a manner which is known in the art and which is therefore not shown in detail, so that it can be adjusted around its center axis M along its circumference. The x-ray system can therefore irradiate a patient, placed on a patient support 5, from different directions in a known manner for locating a zone to be treated with acoustic waves. It is then possible, for example, by adjusting the patient support 5, to position the patient so that the zone to be treated is located in the effective zone of a source 6 of acoustic waves. The source 6 may, for example, be an electromagnetic pressure pulse source which emits focused shockwaves, as disclosed in greater detail, for example, in U.S. Pat. Nos. 4,674,505 and 4,697,588.

For administering treatment, the source 6 assumes a working position as shown in FIG. 1, wherein the source 6 projects from below through an opening 9 in the patient support 5. The opening 9 is disposed in the longitudinal edge of the patient support 5 which faces away from the x-ray locating system, and proceeds at a right angle relative to the plane of the drawing.

Figure 2:
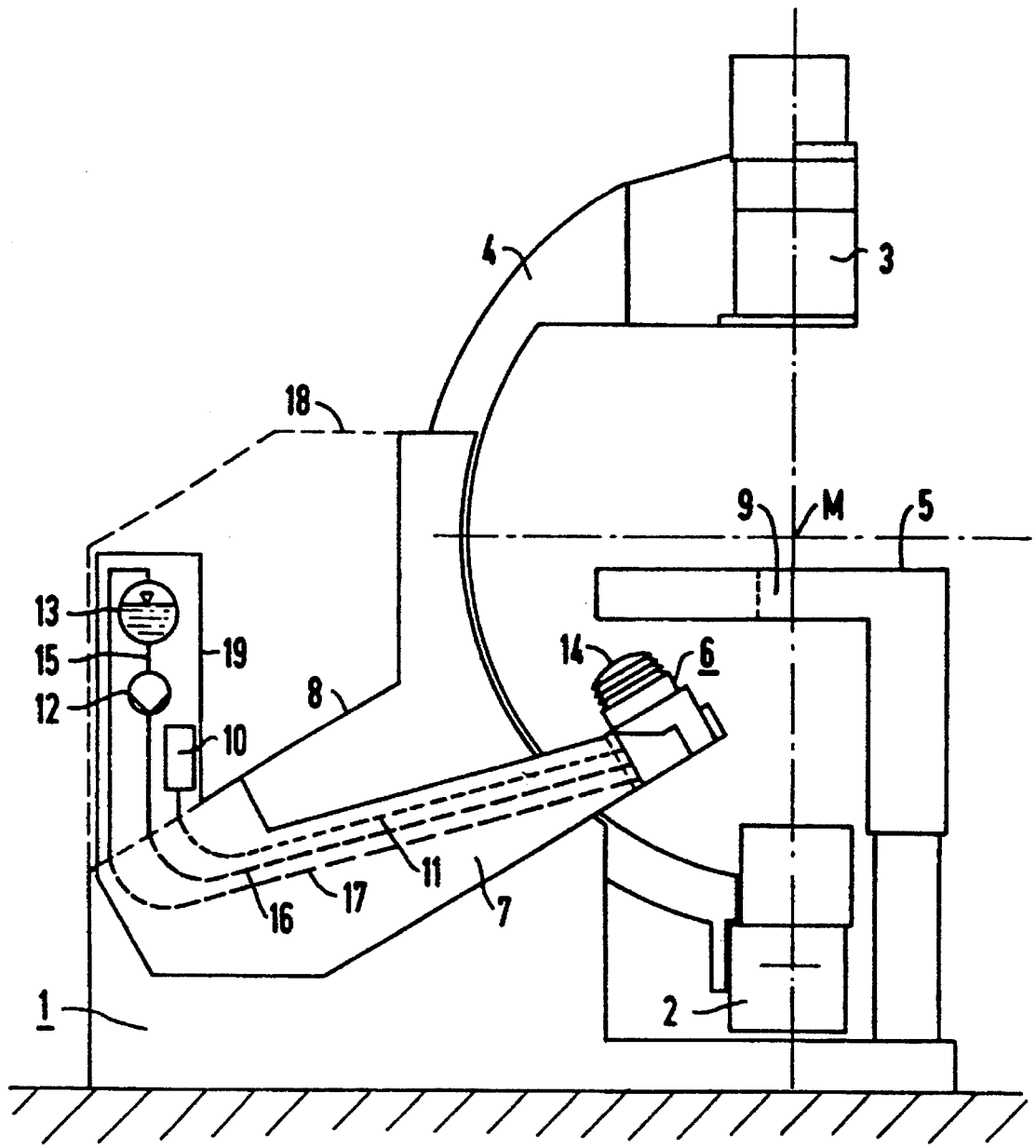
FIG. 2 is an end elevational view of the therapy apparatus of the invention in a second operating condition.

Because the source 6 represents an impediment in its working position when a patient mounts the patient support 5, or is placed thereon, the source 6 is optionally adjustable into a standby position shown in FIG. 2. This is accomplished by motor-adjustment of the position of a carrier 7, to which the source 6 is secured, along an oblique guideway 8 of the base 1. In the exemplary embodiment shown in FIGS. 1 and 2, the adjustment motion ensues on a straight line, however, differently shaped adjustment motions, for example an arcuate motion, are possible.

Guide elements (not shown) such as linear roller bearings are provided between the guideway 8 and the carrier 7.

In order to drive the source 6 for generating acoustic waves, a high-voltage generator 10 is provided which is remote from the source 6 and which is connected thereto via a high-voltage cable 11. In the exemplary embodiment shown in FIGS. 1 and 2, the high-voltage generator 10 is a high-voltage pulse generator.

As is known, the source 6 contains a liquid serving as an acoustic propagation medium for the acoustic waves which are generated. The liquid is circulated, for example, for eliminating heat and to remove gas bubbles. This circulation between a liquid reservoir 13 and the source 6 is accomplished by means of a pump 12. The liquid reservoir 13 is provided in order to compensate for volume fluctuations of the liquid contained in the source 6. Such volume fluctuations arise when the source 6 is pressed against the body surface of the patient by means of a flexible application bellows 14. The pump 12 and the liquid reservoir 13, which are connected to each other via a line 15, are in turn connected to the source 6 via fluid lines 16 and 17.

The high-voltage generator 10, the pump 12 and the liquid reservoir 13 are disposed outside source 6 and thus separated from source 6 by a distance and rigidly connected to the carrier 7 by an assembly mount 19. As a result, neither the distance nor the spatial orientation between the source 6 and the apparatus components consisting of the high-voltage generator 10, the pump 12 and the liquid reservoir 13 changes when the source 6 is adjusted from its working position into its standby position, and vice versa.

No relative motion whatsoever occurs between the aforementioned apparatus components and the source 6, resulting in a high service life for the lines 15, 16 and 17. Moreover, the lines 15, 16 and 17 can be implemented as rigid fluid lines without difficulty, and similarly the stiffness of the high-voltage cable 11 present no difficulty. Simultaneously, enhanced safety is achieved because the risk of damage to the high-voltage cable 11 is reduced.

Additionally, because the high-voltage cable 11 does not have to be coiled or looped in order to accommodate relative movement between the high-voltage generator 10 and the source 6, the length of the high-voltage cable 11 can be made shorter in the therapy apparatus of the invention in comparison to length needed in prior art systems, thereby resulting in lower electrical losses due to this shortened line length. For similar reasons, hydraulic losses due to the length of the lines 15 and 16 are lower in the therapy apparatus of the invention in comparison to prior art systems, which has the advantage of the aforementioned volume compensation ensuing more rapidly in the therapy apparatus of the invention.

If the source 6 is a pressure pulse source of the type disclosed in U.S. Pat. No. 4,697,588, which requires a negative pressure source (under-pressure source) for the operation thereof, the negative pressure source can also be rigidly attached to the carrier 7.

The apparatus can be provided with a cover 18, shown in dashed lines in FIGS. 1 and 2, which covers the volume traversed by the assembly mount 19 between the working and standby positions.

The therapy apparatus of the invention can be employed, for example, for treating stone conditions (lithotripsy), bone conditions (osteotherapy or osteorestoration), tumors, etc. Dependent on the particular medical application, the source 6 may be a pressure pulse source, particularly a shockwave source, an ultrasound source or a cavitation pulse source (under-pressure pulse source).

Although modifications and changes may be suggested by those skilled in the art, it is the intention of the inventors to embody within the patent warranted hereon all changes and modifications as reasonably and properly come within the scope of their contribution to the art.

We claim as our invention:

1. A therapy apparatus comprising:

a base part;

a source of therapeutic acoustic waves for treating the body;

at least one apparatus component for use with said source of therapeutic acoustic waves disposed a fixed distance from, and having a fixed spatial orientation relative to, said source of therapeutic acoustic waves and being connected to said source of therapeutic acoustic waves via a connecting line; and means mounted on said base part for adjusting a position of said source of therapeutic acoustic waves in at least one degree of freedom relative to said base part, said means for adjusting comprising a carrier to which said source of therapeutic acoustic waves and said apparatus component are attached permanently at said fixed distance from each other and permanently in said fixed spatial orientation relative to each other, and said means for adjusting comprising means for adjusting said carrier relative to said base part in said one degree of freedom.

2. A therapy apparatus as claimed in claim 1 wherein said apparatus component comprises a high-voltage generator, and wherein said connecting line comprises a high-voltage cable connecting/said high-voltage generator to said source of therapeutic acoustic waves.

3. A therapy apparatus as claimed in claim 1 wherein said apparatus component comprises a liquid reservoir, and wherein said connecting line comprises a fluid line connecting said liquid reservoir to said source.

4. A therapy apparatus as claimed in claim 3 wherein said fluid line comprises a rigid line.

5. A therapy apparatus as claimed in claim 3 wherein said apparatus component comprises a liquid pump, and wherein said connecting line comprises a fluid line connecting said liquid pump to said source.

6. A therapy apparatus as claimed in claim 5 wherein said fluid line comprises a rigid line.

7. A therapy apparatus as claimed in claim 1 wherein said apparatus component comprises a liquid pump, and wherein said connecting line comprises a fluid line connecting said liquid pump to said source.

8. A therapy apparatus as claimed in claim 7 wherein said fluid line comprises a rigid line.

9. A therapy apparatus as claimed in claim 1 wherein said means for adjusting comprises means for adjusting said source of therapeutic acoustic waves from a standby position to a working position and vis-versa.

10. A therapy apparatus as claimed in claim 1 wherein said means for adjusting comprises means for adjusting said source therapeutic acoustic waves from a standby position to a working position and vis-versa.

11. A therapy apparatus comprising:

a base part;

a source of therapeutic acoustic waves for treating the body;

at least one apparatus component for use with said source of therapeutic acoustic waves disposed a fixed distance from, and having a fixed spatial orientation relative to, said source of therapeutic acoustic waves and being connected to said source of therapeutic acoustic waves via a connecting line; and means mounted on said base part for adjusting a position of said source of therapeutic acoustic waves in at least one degree of freedom relative to said base part, said means for adjusting comprising a carrier to which said source of therapeutic acoustic waves and said apparatus component are attached permanently at said fixed distance from each other and permanently in said fixed spatial orientation relative to each other, and said means for adjusting comprising means for adjusting said carrier relative to said base part in said one degree of freedom, said connecting line being completely contained within said carrier.

12. A therapy apparatus as claimed in claim 11 wherein said apparatus component comprises a high-voltage generator, and wherein said connecting line comprises a high-voltage cable connecting said high-voltage generator to said source of therapeutic acoustic waves.

13. A therapy apparatus as claimed in claim 11 wherein said apparatus component comprises a liquid reservoir, and wherein said connecting line comprises a fluid line connecting said liquid reservoir to said source.

14. A therapy apparatus as claimed in claim 13 wherein said fluid line comprises a rigid line.

15. A therapy apparatus as claimed in claim 13 wherein said apparatus component comprises a liquid pump, and wherein said connecting line comprises a fluid line connecting said liquid pump to said source.

16. A therapy apparatus as claimed in claim 15 wherein said fluid line comprises a rigid line.

17. A therapy apparatus as claimed in claim 11 wherein said apparatus component comprises a liquid pump, and wherein said connecting line comprises a fluid line connecting said liquid pump to said source.

18. A therapy apparatus as claimed in claim 17 wherein said fluid line comprises a rigid line.

* * * * *